United States Patent [19]

Wilhelm

[11] Patent Number: 4,479,967

[45] Date of Patent: Oct. 30, 1984

[54] METHOD OF LOWERING INTRAOCULAR PRESSURE WITH IBUTEROL

[75] Inventor: Max Wilhelm, Watchung, N.J.

[73] Assignee: Ciba-Geigy Corporation, Ardsley, N.Y.

[21] Appl. No.: 430,642

[22] Filed: Sep. 30, 1982

[51] Int. Cl.³ .......................................... A61K 31/225
[52] U.S. Cl. ................................................. 424/313
[58] Field of Search ................. 424/330, 313; 564/365

[56] References Cited

U.S. PATENT DOCUMENTS

| | | | |
|---|---|---|---|
| 3,341,594 | 9/1967 | Thoma et al. | 424/330 |
| 3,775,479 | 11/1973 | Bruderer et al. | 424/330 |
| 3,839,584 | 10/1974 | Hussain et al. | 424/311 |
| 3,937,838 | 2/1976 | Wetterlin et al. | 564/365 |
| 3,954,871 | 5/1976 | Buu-Hoi et al. | 424/330 |
| 4,011,258 | 3/1977 | Wetterlin et al. | 260/479 R |
| 4,145,441 | 3/1979 | Bodor | 424/330 |
| 4,275,074 | 6/1981 | Langham | 424/280 |
| 4,415,564 | 11/1983 | Gamba et al. | 424/244 |

FOREIGN PATENT DOCUMENTS

| | | | |
|---|---|---|---|
| 977088 | 12/1964 | United Kingdom | 564/365 |
| 986048 | 3/1965 | United Kingdom | 564/365 |

OTHER PUBLICATIONS

Hussain et al., Novel Epinepherine Prodrug; J. Pharmaceutical Sciences 65, 1510, (1976).
Wettrell et al., Effect of Beta-Adrenergic Agonists and Antagonists; Exp. Eye Res. 24, 613–619, (1977).
Olsson et al., Pharmacological Properties of KWD 2058; Acta Pharmacol. et Toxicol 35, 76–90, (1974).
Rowland et al., Effects of Adrenergic Drugs; Graefes Archiv Ophthalmologie, 212, 65–75, (1979).
Poulsen et al., Comparison of Ibuterol and Terbutaline in Inhalation Form; Scand J. Respir. Dis. 57, 97–98, (1976).
Johnson et al., Brit. Med. J., Apr. 16, 1977, p. 1006, Ibuterol vs. Terbutaline Inhalation.
Helström et al., Ibuterol and Terbutaline in Asthmatics; Scand. J. Resp. Dis. 58, 247–251, (1977).
Poulsen et al., Ibuterol Hydrodchloride and Terbutaline in Asthma; Brit. Med. J., Apr. 3, 1976, p. 835.
Alm et al., Effect of Prenalterol, Acta Ophthlmologica 59, 882, (1981).
Lasson et al., Comparison of Intravenous Ibuterol (KWD 2058) and Terbutaline, Europ. J. Clin. Pharmcol. 11, 429–433, (1977).
Rowland et al., Adrenergic Drugs and Intraoculr Pressure, Exp. Eye Res. 30, 93–104, (1980).
Potter et al., Adrenergic Drugs and Intraocular Pressure, Exp. Eye Res. 27, 615–625, (1978).
Chemical Abstracts, vol. 84, 159651M, (1976), H. Persson et al., Sympathomimetic Bronchodilating Agents.
Chemical Abstracts, vol. 84, 72204x, (1976), P. Andersson, Bronchospasmolytic and Cardiovascular Effects of Ibuterol and Terbutalinc.

*Primary Examiner*—Douglas W. Robinson
*Attorney, Agent, or Firm*—Norbert Gruenfeld

[57] ABSTRACT

The invention relates to a method of lowering intraocular pressure by a topical application of 2-tert-butylamino-1-(3,5-diisobutyryloxyphenyl)-ethanol or an acid addition salt thereof onto the eye of a mammalian species including man, especially as a conservative and/or curative medical treatment of ocular hypertension and pathological states associated therewith, in the first line glaucoma. The invention also relates to ophthalmic preparations for the topical application comprising an effective amount of the above-identified compounds in combination with a pharmaceutically acceptable carrier, and a method for producing themselves by non-chemical means.

10 Claims, No Drawings

METHOD OF LOWERING INTRAOCULAR PRESSURE WITH IBUTEROL

BACKGROUND OF THE INVENTION

Glaucoma, manifesting itself by the turbidity and opacity of ocular cornea, endangers especially persons of age over 50 and can eventually lead to total blindness. Observations indicate that there is a relation between glaucoma and the intraocular pressure (IOP), and that a pathologically increased IOP, also known as ocular hypertension, is the principal condition for developing glaucoma. In the past, attempts have been made to eliminate, or at least to retard, the progress of the disease by lowering IOP either by surgery or by drug medication.

It is known that in patients treated for various reasons by adrenergic drugs, i.e. drugs exerting a physiological activity toward adrenoreceptors, a lowering of IOP is frequently encountered as a side effect. This decrease in IOP was observed not only with orally administered adrenoreceptor antagonists (especially those blocking $\beta$-receptors such as propranolol and practolol), but also, for not fully understood reasons, with adrenoreceptor agonists, especially $\beta$-adrenergic stimulators such as terbutaline [2-tert-butyl-1-(3,5-dihydroxyphenyl)-ethanol, disclosed in U.S. Pat. No. 4,011,258] which is a potent vaso- and bronchodilator, cf. K. Wettrell et al.: Experimental Eye Research (1977) 24, 613-619 and the references cited therein.

In order to utilize this general effect in ophthalmologic therapeutic practice, especially in control of excessive IOP (i.e. the ocular hypertension) and glaucoma, the primary overall adrenergic effect of an orally administered drug had to be minimized, whereas the desirable "side-effect" onto the eye, i.e. the lowering of IOP, should be retained if not potentiated. Fortunately, animal experiments early indicated that these drugs exert their beneficial effect also by topical administration. On this basis, epinephrine has been widely used anti-glaucoma agent. However, a pervasive side effect of epinephrine therapy is mydriasis, which is unfortunately largely undissociable from the drug's ocular hypotensive action. More recently, epinephrine dipivalic ester, dipivefrin, has undergone extensive development specifically intended for use in ocular hypertension and glaucoma. The substance is about 10 times more potent (i.e. it brings a comparable effect in a 10 times smaller dose) than the parent compound, but is not more efficient than epinephrine in lowering IOP (i.e. the maximum available decrease in IOP irrespectively of doses is the same in both substances). The smaller dose of the ester necessary to lower IOP obviates some of the undesirable extraocular side effects encountered with the relatively high therapeutic doses necessary with epinephrine. The mydriasis, however, as well as other intraocular side effects accompanying epinephrine, are unfortunately likewise present with use of the dipivalate.

A more promising approach was expected by the topical application of the $\beta$-adrenoreceptor stimulators, whose ocular hypertensive effect by oral route has been discussed above. In spite of some controversial results [e.g. a potent $\beta$-adrenergic stimulator prenalterol was found ineffective in lowering IOP in normotensive human eye by oral administration, c.f. A. Alm et al.: Acta Ophthalmologica 59, 882-887 (1981)], it has been generally established that by either oral or topical administration, the decreases in IOP were significantly more pronounced with drugs having strong $\beta_2$-adrenoreceptor stimulating activity, such as isoproterenol, metaproterenol, salbutamol and terbutaline, cf. D. E. Potter and J. M. Rowland: Experimental Eye Research (1978) 27, 615-625. This association of lowering IOP with the adrenergic activity, and especially with the $\beta_2$-receptor-stimulating, vascular activity has been demonstrated also by suppressing experimental ocular hypertension in rabbits, cf. J. M. Rowland and D. E. Potter: Experimental Eye Research (1980) 30, 93-104. An analogous correlation was also found for both normotensive and hypertensive human eye.

In addition to terbutaline, said U.S. Pat. No. 4,011,258 also disclosed corresponding 3',5'-diesters of the parent compound with $C_2$-$C_5$ fatty acids, especially the 3',5'-diisobutyrate, ibuterol, for use as bronchodilators. However, the esters as such have only negligible $\beta_2$-stimulating activity and develop their effect only after having been hydrolyzed in situ by endogenous esterases to form the $\beta_2$-adrenoreceptor-stimulating parent substance terbutaline, see O. A. T. Olsson et al. Acta Pharmacologica et Toxicologica 35, 76 (1974). Hence, the esters, including ibuterol, are bronchodilators of an approximately equal potency as the parent drug, and ibuterol failed to offer the expected advantage over terbutaline when applied as bronchodilator by inhalation in asthmatic patients, see N. McI. Johnson and S. W. Clarke: British Medical Journal 1977, 1006.

In the present invention, the unexpected finding has been made now that ibuterol [1-(3,5-diisobutyryloxyphenyl)-2-tertbutylamino)-ethanol], as compared to the parent terbutaline as standard, reveals surprisingly high effects in lowering IOP by topical application onto a mammal's eye. The experimental data, summarized in Table I, clearly establish that ibuterol not only possesses an increased potency but also an improved efficacy as compared to terbutaline. Whereas this reaches its greatest efficacy in decreasing IOP by approximately 7% at a dose of 100 µl of a 2% solution, IOP reductions amounting more than 10% can be achieved with the same amount (100 µl) of a much more diluted (0.05-0.1%) solution of ibuterol

TABLE 1

| Mean Decrease in IOP 1 Hour After Topical Instil.* | | | |
|---|---|---|---|
| dl-Terbutaline | | Ibuterol Sulfate | |
| ** conc. % | ***IOP-reduction mm Hg ± SE | ** conc. % | ***IOP-reduction mm Hg ± SE |
| 4 | 6.9 ± 0.8 | 0.1 | 9.8 ± 0.8 |
| 2 | 7.1 ± 0.8 | 0.05 | 10.4 ± 0.6 |
| 0.2 | 3.8 ± 0.7 | 0.01 | 6.2 ± 0.9 |
| 0.06 | 3.3 ± 0.9 | 0.005 | 7.7 ± 1.0 |
| 0.02 | 4.7 ± 1.4 | 0.001 | 4.2 ± 1.3 |

*6 rabbits in each experimental group;
**solution in distilled water, concentration calculated as w/v-percentage of free base;
***applied doses 100 µl; SE = standard error

DETAILED DESCRIPTION OF THE INVENTION

Based on these unexpected and surprising results, the present invention relates in the first instance to a method for lowering IOP by the topical application onto the eye of a mammal, inclusive, in particular, the human eye, of a physiologically active amount of ibuterol, preferably in admixture with a therapeutically acceptable carrier, and especially in the form of an ophthalmic preparation. By the topical application, the drug can be brought onto freely accessible surface parts of the eyeball in a manner conventional in ophthalmology, e.g. by applying it in a semi-solid form (such as paste, cream, lotion or gel) or, in particular, in a liquid form (such as eye bath or, especially, eye drops), or also, in a solid form as an ophthalmic insert for a slow drug release. A physiologically effective amount of the drug is such as being capable, on application onto the eye surface of the subject, to bring about an estimable and effective decrease in IOP.

The active principle, i.e. ibuterol, is a compound known per se, which can be used in form of its racemate (±-ibuterol) as of an individual optical isomer thereof. All these forms are applicable both as the free base and as a therapeutically, especially ophthalmically, tolerable acid addition salt. (Owing to the close relationship of ibuterol as the free base and its salts, hereinbefore and hereinafter, the terms "ibuterol" shall, unless specially distinguished, also include the salts thereof, especially pharmaceutically acceptable salts thereof, and the term "salts" shall also include the free base, wherever appropriate.)

Suitable acid addition salts of ibuterol are, in particular, physiologically tolerable salts, preferably those with conventional inorganic and organic acids which are generally known to be capable of producing therapeutically, and in particular, ophthalmically tolerable acid addition salts. Of the inorganic acids, mention should be made of hydrohalic acids (such as hydrobromic and, preferably, hydrochloric acid) as well as oxygen-containing acids (such as, especially, sulfuric, phosphoric and boric acid); of the organic acids, mention should be made especially of sulfonic acids, e.g. carbocyclic, especially aromatic, sulfonic acids (such as (+)-camphor-10-sulfonic, p-toluenesulfonic, p-bromobenzenesulfonic, and benzenesulfonic acid) and alkanesulfonic acids, e.g. $C_1$-$C_7$-lower alkanesulfonic acids (such as, especially, methanesulfonic acid) and also of carboxylic acids, e.g. monobasic alkanoic acids (such as acetic, propionic and lactic acid), polybasic aliphatic acids (such as oxalic, malic, tartaric and citric acid) as well as carbocyclic carboxylic acids (such as benzoic, p-chlorobenzoic, phenylacetic, phenoxyacetic and phthalic acid).

Advantageously, ibuterol is applied to the eyeball in the form of a pharmaceutical preparation conventionally formulated for this purpose. Such a topical ophthalmic preparation comprising a physiologially effective amount of ibuterol or a therapeutically (especially ophthalmically) tolerable acid addition salt thereof together with at least one indifferent carrier, also belongs to the particular embodiments of the invention.

In pharmaceutical preparations for the direct application to the eyeball (such as those mentioned hereinabove), the concentration of ibuterol (calculated as the free base) generally amounts about 0.01 to about 1.0 weight-% (based on the weight of the final composition); a preferred concentration, e.g. in eye drops, is about 0.025 to about 0.5, especially 0.05 to 0.2 % (w/v).

In one embodiment, water is the principal inert carrier, deionized and/or distilled water being used preferably. Advantageously, an aqueous solution of the drug and other ingredients may be used as a stock solution in the manufacture of other, non-homogenous application forms.

In order to prevent the aqueous solutions from the presence of germs of noxious microorganisms, e.g. of those deteriorating or modifying the components and, especially, of pathogenic microorganisms, the primary solutions are preferably sterilized by conventional means (e.g. ultra-filtration and/or heat treatment) and/or rendered preserved, especially by the admixture of preservatives. Common preservatives are applied in usual concentrations (in % w/v), e.g. benzalkonium halides (especially chloride) in an amount of about 0.002 to about 0.02, especially about 0.01%, disodium EDTA, in an amount of about 0.005 to about 0.05, especially about 0.025%, and/or thimerosol in an amount of about 0.0002 to about 0.005, especially about 0.001%. For the chemical stability, the presence of a conventional antioxidant, such as sodium metabisulfite, in an appropriate concentration (such as 0.025 to about 0.25%) is useful and recommendable.

For the ophthalmic tolerability, the pH of the solution should be rendered within the limits of about 5 to about 8, preferably 6.0 to 7.5; advantageously, a constant pH is adjusted by means of a buffer. Therapeutically tolerable and physiologically indifferent buffer components, such as alkali metal acetates, bicarbonates, carbonates and, especially, primary and secondary phosphates, as well as citric acid, are to be used in relatively low concentrations, ordinarily not exceeding 0.05 M, in order to render the solution isotonic, or even more diluted, with respect to tear fluid.

All the above-indicated concentration of the drug and the other ingredients relate to formulations for a direct application to the eyeball, such as, especially, eye drops. In preparations, which are intended for a later dilution, e.g. as a stock solution for an eye bath or as intermediate premixes for preparing other application forms (e.g. semi-solid preparations), the components are mixed in analogous relative proportions, but in an appropriately higher overall concentration.

For a higher ocular comfort in the direct application as eye drops, the solution may be thickened to a viscosity of about 5 to about 20, preferably about 10-15 cps, by adding a conventional thickening agent, such as methylcellulose, hydroxypropylmethylcellulose or polyvinyl alcohol in an appropriate amount.

Also for the ocular comfort, the eye drops can be isotonic with tear fluid; to this effect, an appropriate amount of sodium chloride, or an analogous neutral salt, especially a halide, can be added, or advantageously, the concentration of the buffer component is adjusted such as to meet this condition.

In general, administering of such aqueous solutions of the active component is preferred which have been kept only for a known, limited period of time, e.g. several days or one or two weeks, or, most preferably, have been prepared immediately before the application. To this effect, two-component pharmaceutical preparations are especially useful, i.e. such as consisting of a solid component, preferably one in dosage unit form, which contains the active substance and some of the other solid ingredients, and of a separate solvent component. The actual therapeutic composition is obtained on dissolving the solid component in the solvent component before application, and can be applied in the usual manner in one single treatment or kept for a limited time to be applied in a repeated treatment. The solid-component preparation is preferably formulated into a dosage unit form, especially into tablets, and can contain, beside the active substance, also an antioxidant, buffering compounds, such as those referred to, and/or agents adjusting osmotic pressure and/or viscosity. The solvent component preparation can be water in an appropriate state of purity or an aqueous solution containing e.g. a preservative such as any of those mentioned above, and/or any of the adjuvant ingredients mentioned above, especially those which are liquid or semi-solid or, for any other reason, incompatible with the solid-component preparation, e.g. as being hygroscopic. Advantageously, the relative proportions of the individual ingredients in both the solid and the solvent component are chosen so that a final solution is obtained which in its composition and concentration corresponds to the preferred embodiments specified for the single-component, aqueous preparations; also, an appropriate mutual proportion of the solid and the solvent component may be chosen to the same effect. The dosage units of the solid-component preparation are preferably proportioned so that they provide, dissolved in an appropriate quantity of the solvent component, a quantity of an instantly applicable solution which is sufficient for at least one single administration or, preferably, a multiple administration, e.g. during one day.

Other pharmaceutial preparations applicable for the use in the present invention, such as semi-solid application forms as mentioned above, are also formulated according to methods conventional in pharmaceutical arts and employing conventional ingredients. For continuous release, the active component can also be incorporated or enclosed in a semi-permeable plastic material which is conventionally used for ophthalmologic purposes (such as for ocular inserts, shells and lenses). The incorporation can be effected e.g. by building the drug into a molecular network of a polymer or by impregnating a microporous material with a solution. In the latter instance, e.g. a plastic lens can be kept in an isotonic solution of ibuterol between its regular uses.

The dosage of the active component in a single application is, to a large extent, independent of the body weight or the species of the treated subject, and amounts, for the eye drops of the above-defined composition and concentration range, about 0.03 to 0.15, especially about 0.1 ml to one eyeball. The treatment can be repeated, if necessary, several times, e.g. up to a maximum of 8 applications, in a day. Equivalent dosage is applicable to the other dosage forms.

The invention also relates to the manufacture of the above-defined topical ophthalmic pharmaceutical preparations. The manufacture is effected by conventional non-chemical methods of the art by blending, dissolving or mixing the active component with the other ingredients and, if desired confectioning the primary product into therapeutically applicable final forms.

The following Example, is set forth for purposes of illustration but is in no way intended to limit the scope of the invention thereto.

EXAMPLE

Eye drops containing 0.1% (w/v) ibuterol (calculated as base) are obtained as follows:

One liter of a buffer solution of pH 6.0 (which is 0.00374-molar with respect to citric acid and 0.01252-molar with respect to disodium phosphate) is prepared by mixing 374 ml of a 0.01-molar stock solution of citric acid and 626 ml of a 0.02-molar stock solution of disodium phosphate. In this solution, the following ingredients are dissolved at room temperature in the order as specified (dissolving may be speeded up by stirring provided the contact with atmospheric oxygen is rendered at a minimum):

1.0 g disodium metabisulfite
1.134 g ibuterol sulfate (equivalent to 1.0 g of the free base)
0.1 g benzalkonium chloride
0.25 g disodium EDTA
5.0 g hydroxypropylmethylcellulose This solution is sterilized by fitration to obtain approximately one liter of eye drops of a pH 6.0, which corresponds to 10,000 regular single doses.

In a similar manner, other virtually neutral acid addition salts of ibuterol can be used in quantities corresponding to the amount of the free base. Also, ibuterol base can be used analogously provided that it is neutralized by a molar equivalent of an acid, e.g. citric acid.

It is also possible to add the preservatives (benzalkonium chloride and disodium EDTA) in corresponding quantities to the buffer stock solutions, especially to the citric acid solution, in order to keep them in the preserved condition.

What is claimed is:

1. An intraocular pressure lowering ophthalmic pharmaceutical composition for topical application to the eye of a mammal comprising a sterile isotonic aqueous solution of pH 5-8 comprising about 0.025 to 0.5% of 2-tert-butylamino-1-(3,5-diisobutyryloxyphenyl)-ethanol or an ophthalmically acceptable salt thereof in combination with an ophthalmically acceptable buffering agent as required to maintain pH, an effective concentration of an ophthalmically acceptable preservative and an ophthalmically acceptable neutral salt for adjusting osmotic pressure as required to render the solution isotonic.

2. An ophthalmic pharmaceutical composition according to claim 1 comprising a sterile isotonic aqueous solution of an ophthalmically acceptable salt of 2-tert-butylamino-1-(3,5-diisobutyryloxyphenyl)-ethanol maintained at a pH of 5 to 8.

3. A composition according to claim 2, wherein said aqueous solution contains an ophthalmically acceptable antioxidant and a thickening agent.

4. An ophthalmic pharmaceutical composition according to claim 2 comprising a sterile isotonic aqueous solution of 2-tert-butylamino-1-(3,5-diisobutyryloxyphenyl)-ethanol sulfate maintained at a pH of 5 to 8.

5. A method of lowering intraocular pressure which comprises topically applying to the eye of a mammal in need thereof a therapeutically effective amount of 2-tert-butylamino-1-(3,5-diisobutyryloxyphenyl)-ethanol or an ophthalmically acceptable salt thereof in combination with an ophthalmically acceptable pharmaceutical carrier.

6. A method according to claim 5 wherein said application to the eye is in the form of a semi-solid or liquid ophthalmic pharmaceutical composition.

7. A method according to claim 6 wherein said application to the eye is in the form of an ophthalmic pharmaceutical composition comprising a sterile isotonic aqueous solution of an ophthalmically acceptable salt of 2-tert-butylamino-1-(3,5-diisobutyryloxyphenyl)-ethanol maintained at a pH of 5 to 8.

8. A method according to claim 5 wherein said application to the eye is in the form of a liquid ophthalmic pharmaceutical composition comprising a sterile isotonic aqueous solution of 2-tert-butylamino-1-(3,5-diisobutyryloxyphenyl)-ethanol sulfate maintained at a pH of 5 to 8.

9. A method according to claim 5 wherein said application to the eye is in the form of an ocular insert as the ophthalmic pharmaceutical composition.

10. An intraocular pressure lowering ophthalmic insert for topical application to the eye of a mammal comprising an effective amount of 2-tert-butylamino-1-(3,5-diisobutyryloxyphenyl)-ethanol or an ophthalmically acceptable salt thereof.

* * * * *